US00PP18293P3

(12) United States Plant Patent

Slaughter et al.

(10) Patent No.: US PP18,293 P3

(45) Date of Patent: Dec. 11, 2007

(54) NECTARINE TREE, 'BURNECTWENTYTWO'

(50) Latin Name: *Prunus pesica*
Varietal Denomination: nucipersica

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 11/300,203

(22) Filed: Dec. 13, 2005

(65) Prior Publication Data

US 2007/0136905 P1 Jun. 14, 2007

(51) Int. Cl.
*A01H 5/00* (2006.01)

(52) U.S. Cl. ..... Plt./188

(58) Field of Classification Search ..... Plt./188
See application file for complete search history.

*Primary Examiner*—Kent Bell
*Assistant Examiner*—S. B. McCormick-Ewoldt
(74) *Attorney, Agent, or Firm*—Wells St. John P.S.

(57) ABSTRACT

A new and distinct variety of nectarine tree (*Prunus persica* sub species *nuciperisica*), denominated varietally as 'Burnectwentytwo', and which produces an attractively colored white-fleshed, non-melting, sub-acid clingstone nectarine, which is mature for harvesting and shipment approximately May 25 to June 4 under ecological conditions prevailing in the San Joaquin Valley of central California.

1 Drawing Sheet

BACKGROUND OF THE NEW VARIETY

The present invention relates to a new, novel and distinct variety of nectarine tree, *Prunus persica* (subspecies *nucipersica*), which has been denominated varietally as 'Burnectwentytwo.'

The present variety of nectarine tree resulted from an on-going program of fruit and nut tree breeding. The purpose of this program is to improve the commercial quality of available deciduous fruit and nut varieties, and rootstocks, by creating and releasing promising selections of *prunus, malus* and *regia* species. To this end we make both controlled and hybrid cross pollinations each year in order to produce seedling populations from which improved progenies are evaluated and selected.

The seedling 'Burnectwentytwo' was originated by us from a population of seedlings grown in our experiment orchards located near Fowler, Calif. The seedlings, grown on their own roots, were the result of a controlled cross made in February of 1998, of the yellow-flesh nectarine tree, Crimson Baby (unpatented), which was used as the seed parent; and a sub-acidic white-fleshed, nectarine tree 'Arctic Star' (U.S. Plant Pat. No. 9,332) which was used as the pollen parent. One seedling, identified as 'E45.004' which is the present variety, exhibited especially desirable characteristics, and was marked for subsequent observation. After the 2000 fruiting season, the new, present variety, was selected for advanced evaluation and re-propagation.

ASEXUAL REPRODUCTION

Asexual reproduction of the new and distinct variety of nectarine tree was accomplished by budding the new nectarine tree to 'Nemaguard' Rootstock (unpatented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations.

SUMMARY OF THE VARIETY

'Burnectwentytwo' is a new and distinct variety of nectarine tree, which is considered a regular and productive bearer of relatively firm, sub-acidic white fleshed, non-melting, clingstone fruit which have good flavor and eating quality. The tree of the present variety displays a medium low high chilling requirement of approximately 550 hours. Still further, the present tree also produces relatively uniformly sized fruit throughout the tree. Additionally, the fruit produced by the present tree has a high degree of red skin coloration, a firm flesh, and appears to have good handling and shipping qualities. The 'Burnectwentytwo' nectarine tree bears fruit which are ripe for commercial harvesting and shipment on approximately May 25 to June 4 under the ecological conditions prevailing in the San Joaquin Valley of central California. In relative comparison to the seed parent, the 'Burnectwentytwo' nectarine exhibits white flesh whereas the 'Crimson Baby' exhibits yellow flesh. In relative comparison to the nectarine, 'Arctic Star' (U.S. Pat. No. 9,332), which is the pollen parent and the most similar variety known to the inventors at this time, the present new variety produces fruit which are larger and exhibits a cleaner finish than that produced by the 'Arctic Star'. Further, the date of first harvest of the new variety is 5 days earlier than that of 'Arctic Star'; and the date of full bloom of the new variety is more than 12 days later than that of the variety 'Arctic Star'.

BRIEF DESCRIPTION OF THE DRAWINGS

The accompanying drawing, which is provided, is a color photograph of the new variety of nectarine tree. The photograph depicts two whole mature fruit, and one mature fruit which is dissected substantially at the equatorial plane, viewed from the apical perspective, and exposing the flesh and a portion of the stone. The external coloration of the fruit, as shown, is sufficiently matured for harvesting and shipment. Additionally, the photograph displays a sample vegetative shoot bearing typical leaves, and a typical stone, with the fleshed removed. The colors in the photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and the descriptions as provided hereinafter.

DETAILED DESCRIPTION

Referring more specifically to the pomological details of this new and distinct variety of nectarine tree, the following has been observed during the fourth fruiting season under the ecological conditions prevailing at orchards of the assignee which are located near the town of Fowler, county of Fresno, state of Calif. All major color code designations are by reference to the R.H.S. Colour Chart (Fourth Edition) provided by The Royal Horticultural Society of Great Britain. Common color names are also occasionally used.

Tree:

*Size.*—Generally — Considered medium-large as compared to other common commercial nectarine cultivars ripening in the early season of maturity. The tree of the present variety was pruned to a height of approximately 250.0 cm to about 280.0 cm at commercial maturity.

*Vigor.*—Considered vigorous. The present variety grew from about 150.0 cm to 155.0 cm in height during the first growing season. The new nectarine tree variety was pruned to a height of approximately 150.0 cm during the first dormant season, and primary scaffolds were then selected for the desired tree structure.

*Productivity.*—Productive. Fruit set varies from 2.5 to several times more than the desired crop load. Fruit set is spaced by thinning the tree to develop the remaining fruit into the desired market sized fruit. The number of the fruit set varies with prevailing climatic conditions, and the cultural practices employed during the bloom period, and is therefore not distinctive of this new variety.

*Bearer.*—Regular. Fruit set has been heavy, and thinning of the tree was necessary during the past 4 years.

*Form.*—Upright, and pruned into a vase shape.

*Density.*—Considered medium dense. It has been discovered that pruning the branches from the center of the tree to obtain a resulting vase shape allows for proper air movement in the tree, and appropriate amounts of sunlight to enhance fruit color and renewal of fruiting wood throughout the tree.

*Hardiness.*—The present tree was grown and evaluated in USDA Hardiness Zone 9. Winter chilling requirements of the new tree are approximately 550 hours below 7.0 degrees C. The variety appears to be hardy under typical central San Joaquin Valley climatic conditions.

Trunk:

*Diameter.*—Approximately 13.0 cm in diameter when measured at a distance of approximately 15.24 cm above the soil level. This measurement was taken at the end of the fourth growing season.

*Bark texture.*—Considered moderately rough, with numerous folds of papery scarfskin being present.

*Lenticels.*—Numerous flat, oval lenticels are present. The lenticels range in size from approximately 4.0 to about 9.0 millimeters in width; and from about 1.0 to about 2.0 millimeters in height.

*Lenticel color.*—Considered an Orange Brown, (RHS Greyed-Orange Group 166 C).

*Bark coloration.*—Variable, but it is generally considered to be gray-brown, (RHS Greyed-Orange Group 177 A).

Branches:

*Size.*—Considered medium for the variety.

*Diameter.*—Average as compared to other nectarine tree varieties. The branches have a diameter of about 6.8 centimeters when measured during the fourth year after grafting.

*Surface texture.*—Average, and appearing furrowed on wood which is several years old.

*Crotch angles.*—Primary branches are considered variable between about 46 to about 53 degrees from the horizontal axis. This particular characteristics is not considered distinctive of the variety, however.

*Current season shoots.*—Surface texture — Substantially glabrous.

*Internode length.*—Approximately 2.5 to about 2.8 cm. This tree characteristic is highly dependent upon plant nutrition, soil quality, pruning and tree care and therefore is not distinctive of the variety.

*Color of mature branches.*—Medium brown, (RHS Greyed-Orange 174 A).

*Current seasons shoots.*—Color. — Light green, (RHS Yellow-Green Group 143 A). The color of new shoot tips is considered a bright and shiny green (RHS Green Group 141 B).

Leaves:

*Size.*—Considered medium-large for the species. Leaf measurements have been taken from vigorous, upright, current-season growth, at approximately mid-shoot.

*Leaf length.*—Approximately 155.0 to about 170.0 millimeters.

*Leaf width.*—Approximately 35.0 to about 38.0 millimeters.

*Leaf base shape.*—Slightly oblique relative to the leaf longitudinal axis.

*Leaf form.*—Lanceloate.

*Leaf tip form.*—Acuminate.

*Leaf color.*—Upper surface — Dark green, (approximately RHS Green Group 139 A).

*Leaf texture.*—Glabrous.

*Leaf color.*—Lower surface. — Medium green, (RHS Green Group 137 B).

*Leaf venation.*—Pinnately veined.

*Mid-Vein.*—Color. — Light yellow green, (RHS Yellow-Green Group 150 D).

*Leaf margins.*—Slightly undulating.

*Form.*—Considered crenate, occasionally doubly crenate.

*Uniformity.*—Considered generally uniform.

*Leaf petioles.*—Size. — Considered medium long. Length. — about 7.0 to about 9.0 mm. Diameter. — about 2.0 to about 2.5 mm. Color. — Pale green, (RHS Yellow-Green Group 150 C).

*Leaf glands.*—Size. — About 1.0 mm in height, and about 1.0 mm in width. Number. — Generally one per side, occasionally two per side. Type: — Reniform, considered reasonably appressed relative to the petiole margin and considered small. The glands on more mature leaves are occasionally senescent. The leaves are early deciduous.

*Color.*—Orange brown, (RHS Grey-Brown Group N199 C).

*Leaf stipules.*—Size. — Medium for the variety. Number. — Typically 2 per leaf bud, and up to 6 per shoot tip. Form. — Lanceolate in form, and having a serrated margin. Color. — Green, (RHS Green Group 141 B) when young, but graduating to a brown color, (RHS Greyed-Orange group 165 A) with advancing senescence. The stipules are considered to be early deciduous.

Flower:

*Flower buds.*—Generally — The floral buds, depending upon the stage of development, are approximately 8.0 millimeters wide; and about 13.0 millimeters long; conic in form; and slightly appressed relative to the bearing shoot.

*Flower buds.*—Color — The bud scales are reddish-brown, (approximately RHS Greyed Purple Group 183 B). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not available.

*Date of first bloom.* — Feb. 23, 2005.

*Blooming time.*—considered early mid-season in relative comparison to other commercial nectarine cultivars grown in the central San Joaquin Valley. Date of full bloom was observed on Mar. 4, 2003. The date of bloom varies slightly with the prevailing climatic conditions, and cultural practices.

*Duration of bloom.*—Approximately 10 days. This characteristic varies slightly with climatic conditions.

*Flower type.*—The variety is considered to have a showy type flower.

*Flower size.*—Flower diameter at full bloom is approximately 45.0 to about 50.0 millimeters.

*Bloom quantity.*—Considered very abundant.

*Flower bud frequency.*—Normally 1 to 2 flower buds appear per node. Rarely 3 buds per node may be observed.

*Petal size.*—Generally — Considered large for the species.

*Length.*—Approximately 20.0 to about 24.0 millimeters.

*Width.*—Approximately 18.0 to about 21.0 millimeters.

*Petal form.*—Rotund.

*Petal count.*—Generally 5. Occasionally individual flower pedal counts are doubled.

*Petal texture.*—Glabrous.

*Petal color.*—Light pink, (RHS Red-Purple Group 62 C) to a medium pink, (RHS Red-Purple Group 63 C).

*Fragrance.*—Slight.

*Petal claw.*—Form. — The claw is considered truncate in shape, and has a large size when compared to other varieties. Length. — Approximately 9.0 to about 11.0 millimeters. Width. — Approximately 7.0 to about 9.0 millimeters.

*Petal margins.*—Generally considered variable, from nearly smooth, to moderately undulate.

*Petal apex.*—Generally — The petal apices generally appear entire and without an apical groove.

*Flower pedicel.*—Length. — Considered medium-long, and having an average length of approximately 4.0 to about 5.0 millimeters. Diameter. — Considered average, approximately 3.0 millimeters. Color. — A pale green, (RHS Greyed Green Group 195 A).

*Floral nectaries.*—Color. — A light green, (RHS Green Group 141 C).

*Calyx.*—Surface Texture. — Generally glabrous. Color. — A dull red, (approximately RHS Greyed-Purple Group 187 B).

*Sepals.*—Surface texture. — The surface has a short, fine, pubescent texture. Size. — Average, and ovate in form, and having a length of about 5 mm. and a width of about 3.5 mm. Color. — A dark reddish purple, (approximately RHS Greyed-Purple Group 187 A).

*Anthers.*—Generally. — Large in size. Color. — Red to reddish purple, (approximately RHS Greyed-Purple Group 187 D).

*Pollen production.*—Pollen is abundant, and has a yellow color, (approximately RHS Yellow Group 11 A). The present variety is self-pollinating.

*Filaments.*—Size. — Variable in length, approximately 17.0 to about 20.0 millimeters in length. Color. — Considered a pale pink, (RHS Red-Purple Group 65 C).

*Pistil.*—Number. — Usually 1, rarely 2. Generally. — Large in size. Length. — Approximately 18.0 to about 22.0 millimeters including the ovary. The ovary has glabrous surface texture. Color. — Considered a very pale green, (approximately RHS Yellow-Green Group 145 C). Surface Texture. — The variety has a long glabrous pistil.

Fruit:

*Maturity when described.*—Firm ripe condition (shipping ripe). Date of first picking. — May 25, 2005. Date of last picking. — Jun. 4, 2005. The date of harvest varies slightly with climatic conditions and crop load.

*Size.*—Generally — Considered relatively large, and uniform.

*Average cheek diameter.*—Approximately 70.0 to about 75.0 millimeters.

*Average axial diameter.*—Approximately 68.0 to about 71.0 millimeters.

*Typical weight.*—Approximately 208.0 grams. This characteristics is highly dependent upon cultural practices, and therefore is not particularly distinctive of this new variety.

*Fruit form.*—Globose — Shaped. The fruit is generally uniform in symmetry.

*Fruit suture.*—Shallow, and extending from the base to apex. No apparent callousing or stitching exists along the suture line.

*Suture.*—Color — The background color appears to be white, (approximately RHS White Group 155 C), with occasional red coloration, (approximately RHS Red Group 46 C).

*Ventral surface.*—Form — Full, to slightly extended.

*Apex.*—Rounded.

*Base.*—Retuse.

*Stem cavity.*—Rounded and relatively shallow. The average depth of the stem cavity is about 1.0 cm. The average width of the stem cavity is about 1.2 cm.

*Fruit skin.*—Thickness. — Considered medium in thickness, and tenacious to the flesh. Texture. — Glabrous. Taste. — Non-astringent. Tendency to crack. — A rare incidence of cracking has been observed. Occasional russetting can be observed in some years.

*Color.*—Blush Color. — The blush color is variable from a medium red, (approximately RHS Red Group 45B); to a dark red, (approximately RHS Greyed-Purple Group 183 B). Blush color ranges from 75% to about 95% of the fruit surface depending upon the amount of sunlight exposure and the prevailing growing conditions. Ground Color. — Generally a light yellow, (approximately RHS White Group 155 C).

*Fruit stem.*—Moderate in lengthy, approximately 5.0 to about 7.0 millimeters.

*Diameter.*—Approximately 2.0 to about 3.0 millimeters.

*Color.*—Light tan, (approximately RHS Greyed-Orange Group 164 D).

*Flesh.*—Ripens. — Evenly. Texture. — Firm, and dense. Considered non-melting. Fibers. — Few, small, and tender ones are found. Aroma. — Slight. Eating Quality. — Considered very good. Flavor. — Considered sweet and sub-acidic. The flavor is considered pleasant. Juice. — Moderate. Brix. — About 15.5 degrees. This characteristic varies slightly with the number of fruit per tree; the prevailing cultural practices; and the surrounding climatic conditions. Flesh color. — Pale white, (approximately RHS White Group 155 C).

Stone:

*Type.*—Clingstone.

*Size.*—Considered medium for the variety. The stone size varies with the resulting crop load, and tree vigor, and is therefore is not considered a distinguishing characteristic of this new variety.

*Length.*—Average, about 24.5 to about 29.0 millimeters.

*Width.*—Average, about 23.0 to about 25.0 millimeters.

*Diameter.*—Average, about 17.0 to about 22.0 millimeters.

*Form.*—Ovoid.

*Base.*—The stone is usually rotund relative to the stone's vertical axis.

*Apex.*—Shape — The stone apex has a raised tip.

*Stone surface.*—Surface texture. — The surface texture is characterized generally by a concentric ridge/furrow pattern which begins at the margins and drooping toward the apical tip. Substantial grooving over the apical shoulders is evident. Surface pitting is less generally noted than ridges or furrows, but is more frequently observed in the mid-section of the stone. Ridges. — The surface texture varies from sharp to rounded. Ventral Edge. — Width — Considered medium, and having a dimension of approximately 2.0 to about 4.0 millimeters when measured at the mid-suture. The wings are most prominent over the suture line. Occasionally a lower ridge will extend outside of the stone margin, and along the ventral edge. Dorsal Edge. — Shape. — Full, heavily grooved, and having a relatively smooth edge.

*Stone color.* — The color of the dry stone is a pale orange (Greyed-Orange Group approximately RHS 170 D).

*Tendency to split.*—Occasional splits have been noted.

*Kernel.*—Generally — The kernel is considered immature and semi-gelatinous.

*Form.*—Considered ovoid.

*Pellicle.*—Pubescent.

*Color.*—Considered to be a pale brown (Yellow-White Group 158 A).

*Use.*—The subject variety 'Burnectwentytwo' is considered to be a Nectarine tree which matures early in the season, and which produces fruit, which are considered firm, attractively colored, and which re useful for both local and long distance shipping.

*Keeping quality.*—Excellent. Fruit has stored well for up to 25 days after harvest at 1.0 degree Celsius.

*Shipping quality.*—Good. The fruit of the new nectarine tree variety showed minimal bruising of the flesh, or skin damage, after being subjected to normal harvest and packing procedures.

*Resistance to insects and disease.*—No particularly susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure to Plant Letters Patent is:

1. A new distinct variety of nectarine tree, substantially as illustrated and described, and which is characterized principally as to novelty to producing an attractively colored, white-fleshed, non-melting, sub-acid clingstone nectarine which is mature for harvesting and shipment approximately May 25 to June 4 under the ecological conditions prevailing in the San Joaquin Valley of central California.

* * * * *

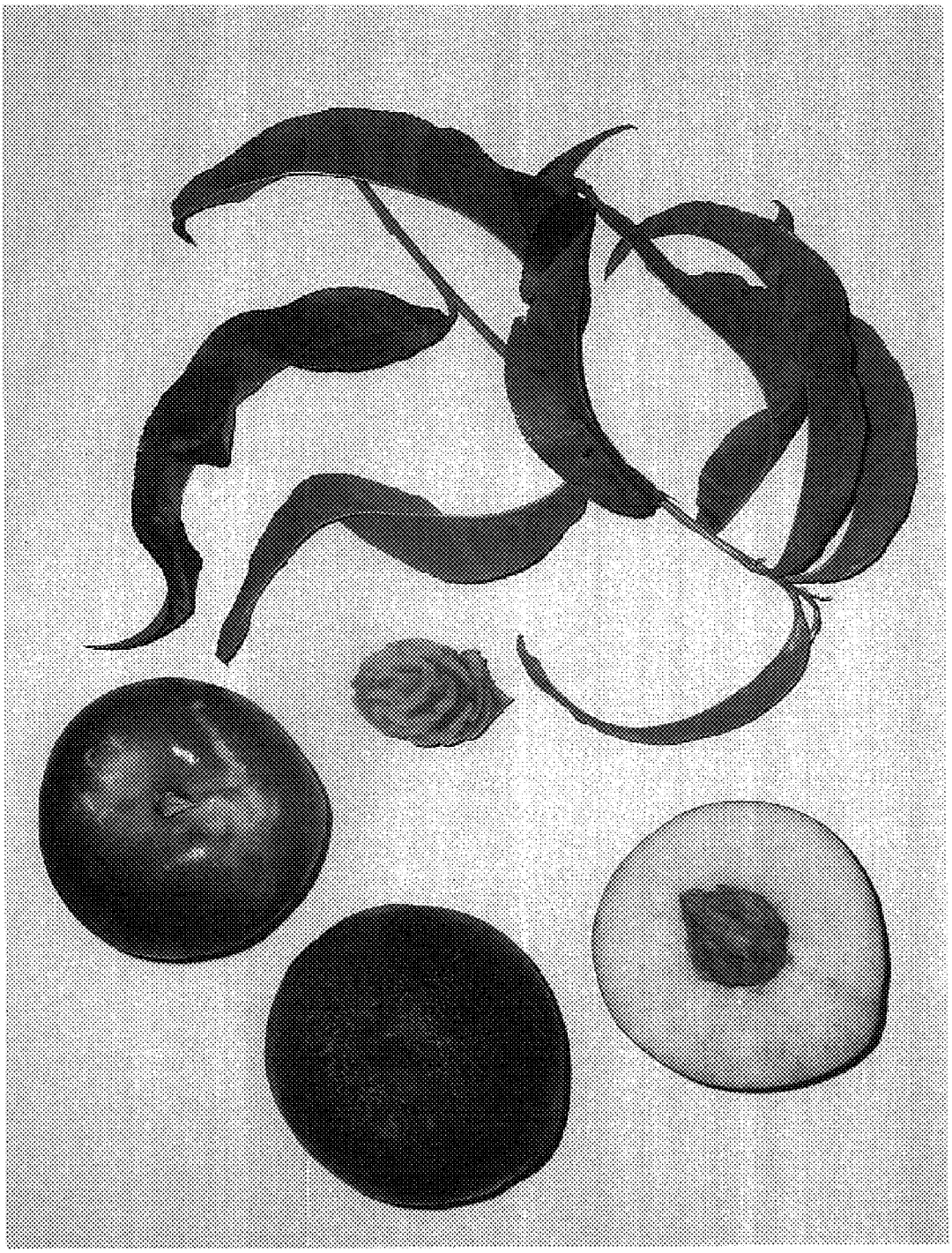

UNITED STATES PATENT AND TRADEMARK OFFICE

CERTIFICATE OF CORRECTION

PATENT NO. : PP 18,293 P3
APPLICATION NO. : 11/300203
DATED : December 11, 2007
INVENTOR(S) : John K. Slaughter et al.

It is certified that error appears in the above-identified patent and that said Letters Patent is hereby corrected as shown below:

Column 7, line 23, Fruit Stem, replace “lengthy” with --length--.

Column 8, line 23, Use, replace “which re” with --which are--.

Column 8, line 46, paragraph before Claim 1, replace “secure to” with --secure by--.

Signed and Sealed this

Eighth Day of July, 2008

JON W. DUDAS
*Director of the United States Patent and Trademark Office*